US012629504B2

(12) United States Patent
Na et al.

(10) Patent No.: US 12,629,504 B2
(45) Date of Patent: May 19, 2026

(54) NEEDLE ASSEMBLY, SKIN STIMULATOR INCLUDING THE SAME, AND MANUFACTURING METHOD THEREOF

(71) Applicant: VIOL CO., LTD., Seongnam-si (KR)

(72) Inventors: Jongju Na, Seoul (KR); Heeyoung Lee, Suwon-si (KR); Dongkeun Shin, Anseong-si (KR)

(73) Assignee: SERENDIA, LLC, Lake Forest, CA (US)

( * ) Notice: Subject to any disclaimer, the term of this patent is extended or adjusted under 35 U.S.C. 154(b) by 1192 days.

(21) Appl. No.: 17/616,730

(22) PCT Filed: May 22, 2020

(86) PCT No.: PCT/KR2020/006727
§ 371 (c)(1),
(2) Date: Dec. 6, 2021

(87) PCT Pub. No.: WO2020/251188
PCT Pub. Date: Dec. 17, 2020

(65) Prior Publication Data
US 2022/0323734 A1 Oct. 13, 2022

(30) Foreign Application Priority Data

Jun. 11, 2019 (KR) ........................ 10-2019-0068966

(51) Int. Cl.
*A61M 37/00* (2006.01)
*A61N 1/05* (2006.01)
*A61N 1/32* (2006.01)

(52) U.S. Cl.
CPC ....... *A61M 37/0015* (2013.01); *A61N 1/0502* (2013.01); *A61N 1/325* (2013.01);
(Continued)

(58) Field of Classification Search
CPC ...... A61M 37/0015; A61M 2037/0007; A61M 2037/0023; A61M 2037/0046; A61M 2037/0053; A61M 37/00; A61M 2037/0061; A61N 1/0502; A61N 1/325; A61N 1/0428; A61N 1/328;
(Continued)

(56) References Cited

U.S. PATENT DOCUMENTS

| | | | |
|---|---|---|---|
| 8,666,487 | B2 | 3/2014 | Kang |
| 2003/0083645 | A1 | 5/2003 | Angel et al. |

(Continued)

FOREIGN PATENT DOCUMENTS

| | | |
|---|---|---|
| CN | 101507857 | 8/2009 |
| CN | 108367143 | 8/2018 |

(Continued)

OTHER PUBLICATIONS

EPO, Search Report of EP 20823241.3 dated May 15, 2023.

*Primary Examiner* — Laura A Bouchelle
*Assistant Examiner* — Sarah Dympna Grasmeder
(74) *Attorney, Agent, or Firm* — LEX IP MEISTER, PLLC

(57) ABSTRACT

Provided is a needle assembly including: a plurality of needles; a main body having a plurality of holes through which the plurality of needles pass in a first direction; and a fixing member coupled to the main body and having a plurality of fixed inclined surfaces supporting the plurality of needles.

13 Claims, 12 Drawing Sheets

(52) U.S. Cl.
CPC ............... *A61M 2037/0007* (2013.01); *A61M 2037/0023* (2013.01); *A61M 2037/0046* (2013.01); *A61M 2037/0053* (2013.01)

(58) Field of Classification Search
CPC .... A61N 1/36017; A61N 1/0476; A61N 1/30; A61N 1/303; A61N 1/04
See application file for complete search history.

(56) References Cited

U.S. PATENT DOCUMENTS

| | | | |
|---|---|---|---|
| 2006/0206164 A1 | 9/2006 | Gavronsky | |
| 2010/0121307 A1 | 5/2010 | Lockard et al. | |
| 2014/0222105 A1* | 8/2014 | Broderick | A61N 1/0412 607/59 |

| | | | | |
|---|---|---|---|---|
| 2016/0082239 A1* | 3/2016 | Tamaru | | A61M 37/0015 604/173 |
| 2016/0354589 A1 | 12/2016 | Kobayashi et al. | | |

FOREIGN PATENT DOCUMENTS

| | | | |
|---|---|---|---|
| JP | 2012-157406 | 8/2012 | |
| JP | 2014-524796 | 9/2014 | |
| KR | 10-2012-0111851 | 10/2012 | |
| KR | 20-2012-0007011 | 10/2012 | |
| KR | 10-2012-0130314 | 11/2012 | |
| KR | 10-1423590 | 7/2014 | |
| KR | 10-2015-0018336 | 2/2015 | |
| KR | 10-2019-0057094 | 5/2019 | |
| WO | 2014/178140 | 11/2014 | |
| WO | 2018/174454 | 9/2018 | |
| WO | WO-2018174454 A1 * | 9/2018 | A61M 37/00 |

* cited by examiner

NEEDLE ASSEMBLY, SKIN STIMULATOR INCLUDING THE SAME, AND MANUFACTURING METHOD THEREOF

TECHNICAL FIELD

The present invention relates to a needle assembly, a skin stimulator including the same, and a manufacturing method of the skin stimulator.

BACKGROUND ART

Human skin may mainly include three layers of an epidermal layer, a dermal layer and a subcutaneous tissue layer. The human skin may be the largest protective organ protecting a human body from an external environment and continuously repeating its fallout and reproduction. The epidermal layer may include four layers of a stratum corneum layer, a granular layer, a spinous layer and a basal layer, and the dermal layer may include collagen and elastin connective tissue between a capillary and a fiber. Keratinocytes may be made in the basal layer and ascend to the stratum corneum layer every 28 days. As a human gets older, a human skin cell may have a slower reproduction cycle to cause his/her aging to be in progress.

The stratum corneum layer may have a thickness of about 0.1 to 0.2 mm and may be a dead cell layer having little ability to absorb a substance. Therefore, when the stratum corneum layer is pierced to make a micro-channel, the substance may penetrate through the epidermal layer to the dermal layer to be effectively absorbed thereinto.

For anti-wrinkle or elastic skin, nutrients such as vitamin C and peptide, necessary for producing the collagen have been applied or sprayed to the skin. However, this method is not effective because the supplied nutrients are difficult to penetrate through the stratum corneum layer of the skin. A skin stimulator including a plurality of needles may usually be used to solve this problem.

The needle of the skin stimulator may stimulate the skin to produce the elastin and the collagen, and may increase a ratio at which a medicine substance and a cosmetic ingredient are absorbed into the skin, through the micro-channel made by the needle. Therefore, the skin stimulator may reduce various skin troubles without peeling or a surgery.

Korean Patent No. 10-1160097 discloses a manufacturing method of a multi-needle for a skin procedure in which the needle is inserted into a main body having a plurality of holes and then completely fixed to the main body by using a chemical curing agent. However, when the needle is fixed by using such an adhesive, a worker may be exposed to a harmful substance due to the chemical curing agent, and productivity may be lower due to a condition such as curing time.

In addition, Korean Utility Model No. 20-0468393 discloses a plurality of micro-needles which are inserted into coupling holes formed in one surface of a stamp having the plurality of coupling holes, thereby making their tip portions protrude to the other surface of the stamp by a predetermined length. However, when inserted into the coupling holes in pillar-shaped protrusions formed on the stamp, the plurality of micro-needles may be difficult to be completely fixed to the stamp. Therefore, the needles may be pushed out or come out when used.

DISCLOSURE

Technical Problem

An exemplary embodiment of the present invention provides a needle assembly to which a plurality of needles are firmly fixed and in which a chemical curing agent is not used, thereby having increased safety in a human procedure and improved economic feasibility of the manufacturing process, a skin stimulator including the same, and a manufacturing method of the skin stimulator.

Technical Solution

According to an exemplary embodiment of the present invention, a needle assembly includes: a plurality of needles; a main body having a plurality of holes through which the plurality of needles pass in a first direction; and a fixing member coupled to the main body and having a plurality of fixed inclined surfaces supporting the plurality of needles.

The plurality of needles may be supported on the plurality of fixed inclined surfaces and bent along the plurality of fixed inclined surfaces.

The plurality of fixed inclined surfaces may be respectively formed at positions corresponding to the plurality of holes.

The fixing member may include an outer frame coupled to the main body and a plurality of inner frames disposed parallel to and spaced apart from each other inside the outer frame, and the plurality of fixed inclined surfaces may be formed on both side surfaces of each of the plurality of inner frames.

The outer frame may include a pair of long sides and a pair of short sides, respectively facing each other, the plurality of inner frames may extend to connect the pair of long sides or pair of short sides of the outer frame to each other, and the plurality of fixed inclined surfaces may each be inclined by a first inclination angle in a second direction in which the plurality of inner frames extend when viewed in the first direction.

The plurality of inner frames may include a first inner frame and a second inner frame, which are adjacent to and opposite to each other, the plurality of fixed inclined surfaces may include a first fixed inclined surface and a second fixed inclined surface respectively formed on opposite side surfaces of the first inner frame and the second inner frame, and second inclination angles respectively formed by the first fixed inclined surface and the second fixed inclined surface in the first direction may have the same absolute value as each other.

A first needle bent along the first fixed inclined surface may be parallel to a second needle bent along the second fixed inclined surface.

The main body may include a flat main body having the plurality of holes, and a side wall portion extending from an edge of the flat main body to form an accommodation space accommodating the fixing member and having a plurality of coupling holes, and a first coupling protrusion coupled to at least one of the plurality of coupling holes may be formed outside the fixing member.

According to another exemplary embodiment of the present invention, a skin stimulator includes: a needle assembly including a plurality of needles, a flat main body having a plurality of holes through which the plurality of needles pass in a first direction, and a fixing member coupled to the main body and having a plurality of fixed inclined surfaces supporting the plurality of needles; a housing having an inner space in which the needle assembly is seated; and a handle detachably coupled to the housing.

The needle assembly may have a plurality of coupling holes coupling the needle assembly to the housing, and a second coupling protrusion coupled to at least one of the plurality of coupling holes may be formed inside the housing.

The housing may include a housing frame forming the inner space, and an electrode unit installed in the housing frame and disposed on the same plane as a surface of the flat main body.

The electrode unit may include a positive electrode unit and a negative electrode unit respectively positioned on both sides of the needle assembly.

The handle may include a power supply unit supplying power to the electrode unit.

According to another exemplary embodiment of the present invention, a manufacturing method of a skin stimulator includes: positioning a main body having a plurality of holes on a jig; inserting a plurality of needles into the plurality of holes; coupling a fixing member to the main body while pressing the plurality of needles by using the fixing member; coupling a needle assembly, in which the fixing member and the main body are coupled to each other, to a housing; and detachably fastening a handle to the housing.

The fixing member may have a plurality of fixed inclined surfaces respectively formed at positions corresponding to the plurality of holes, and in the coupling of the fixing member to the main body, the plurality of needles may be bent along and fixed to the plurality of fixed inclined surfaces.

Advantageous Effects

According to an exemplary embodiment of the present invention, the needle assembly to which the plurality of needles are fixed using the fixing member without a chemical curing agent harmful to the human body, the skin stimulator including the same, and the manufacturing method of the skin stimulator may have the increased safety in the human procedure and the reduced environmental factor harmful to a process worker.

In addition, a chemical curing agent such as a conventional epoxy may have low economic feasibility due to curing time of 24 hours or more. However, the present invention does not use such a separate chemical curing agent to have shorter manufacturing time, thus having an improved process.

In addition, when using the chemical curing agent, some needles may have changed positions due to shrinkage occurring while the chemical curing agent is cured. However, the present invention may allow the plurality of needles to be inserted to the predetermined depth.

In addition, when using the chemical curing agent, a cover may be required to cover the chemical curing agent. However, the present invention does not use the chemical curing agent, and thus does not require any separate cover.

MODE FOR INVENTION

The present invention will be described more fully hereinafter with reference to the accompanying drawings, in which exemplary embodiments of the present invention are shown. As those skilled in the art would realize, the described exemplary embodiments may be modified in various different ways, all without departing from the scope of the present invention.

Figure 1:
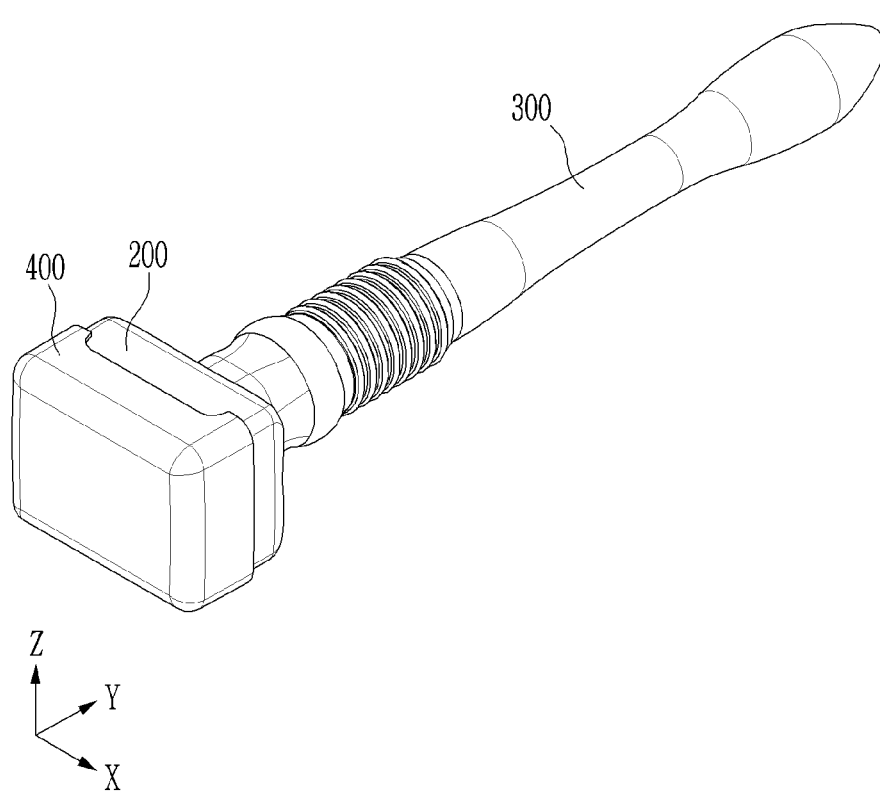
FIG. 1 is a schematic perspective view of a skin stimulator according to an exemplary embodiment of the present invention.
Figure 2:
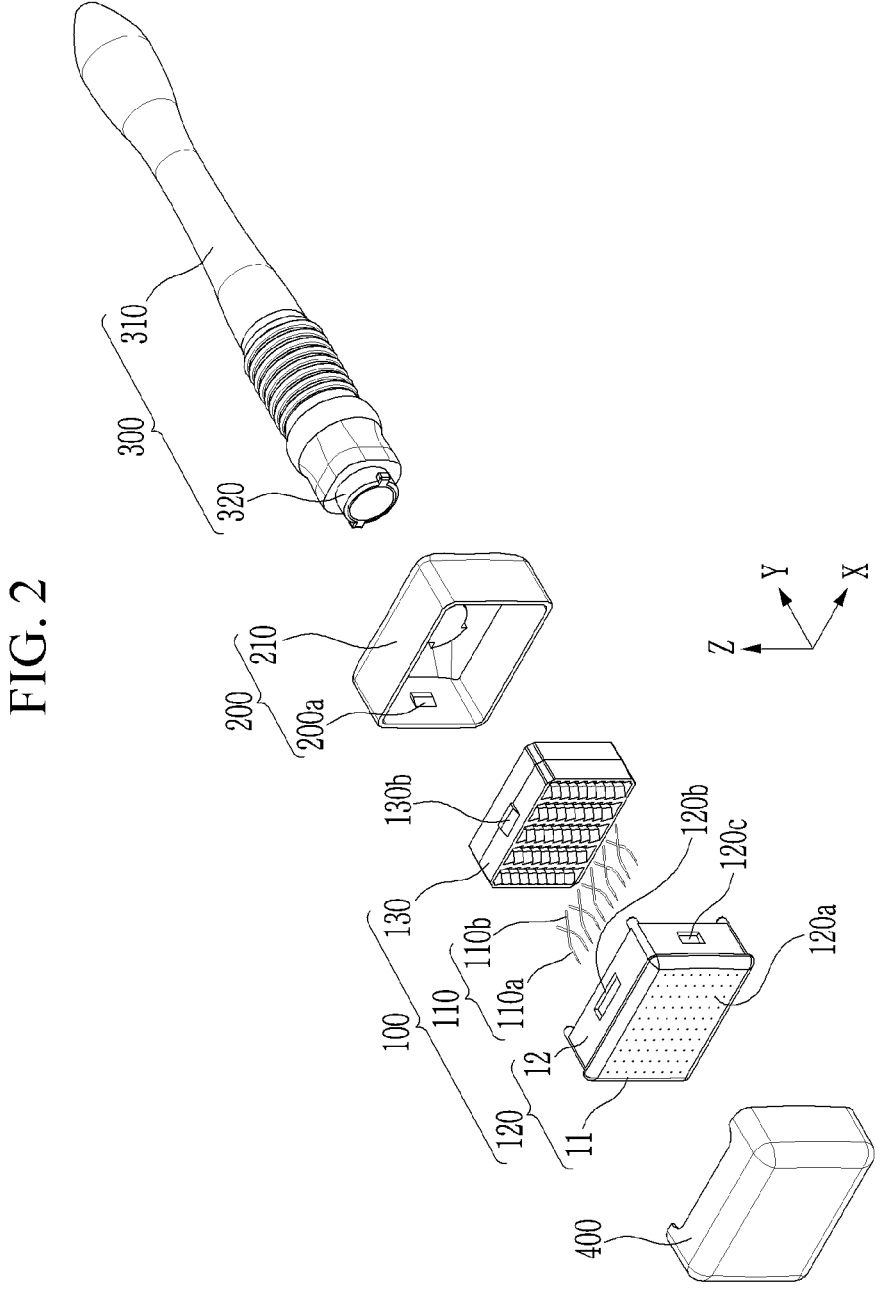
FIG. 2 is an exploded perspective view of the skin stimulator according to an exemplary embodiment of the present invention.

FIG. 1 is a schematic perspective view of a skin stimulator according to an exemplary embodiment of the present invention; and FIG. 2 is an exploded perspective view of the skin stimulator according to an exemplary embodiment of the present invention.

As shown in FIGS. 1 and 2, the skin stimulator according to an exemplary embodiment of the present invention may include a needle assembly 100 having a plurality of needles 110, a housing 200 seating the needle assembly 100 therein, a handle 300 detachably coupled to the housing 200 and an assembly cover 400 covering the needle assembly 100.

The assembly cover 400, the needle assembly 100, the housing 200 and the handle 300 may be sequentially arranged in a first direction Y.

The needle assembly 100 may include the plurality of needles 110, a main body 120, and a fixing member 130.

The plurality of needles 110 may have the same length as each other and may be made of a metal material. Each needle 110 may have a length of about 8 mm to 12 mm and a diameter of about 0.3 mm. A sharp tip portion of the plurality of needles 110 may pierce a stratum corneum layer of human skin supposed to get a medical procedure to make a micro passageway in the skin. In this manner, the needle 110 may assist a substance to penetrate through an epidermal layer to a dermal layer and to be effectively absorbed thereinto.

The main body 120 may include a flat main body 11 having holes 120a, and a side wall portion 12 extending from an edge of the flat main body 11.

The plurality of needles 110 may be inserted through the plurality of holes 120a formed in the flat main body 11 in the first direction Y. The plurality of holes 120a may be spaced apart from each other by a predetermined distance to form a lattice shape. In this exemplary embodiment, the plurality of holes 120a are arranged in the lattice shape, and is not limited thereto. The holes may be arranged in various shapes throughout the flat main body 11.

The tip portion of the needle 110 may protrude from one surface of the flat main body 11 of the main body 120, having the hole 120a, within a range of 0.2 mm to 0.24 mm.

When having a protrusion length smaller than 0.2 mm, the tip portion of the needle 110 may be difficult to be supported by a jig (G, see FIG. 10), and may thus be impossible to have the constant protrusion length. In this case, the needle is difficult to be inserted into the main body 120 while maintaining a vertical state to the main body 120, thereby making the fixing member 130 difficult to be coupled to the main body 120. On the other hand, when having a protrusion length greater than 0.24 mm, the tip portion of the needle 110 may be inserted through the stratum corneum layer to a significant portion of the epidermal layer, which may cause pain. It is thus preferable to perform the procedure without causing the pain in the above protrusion range. However, the protrusion length may be made greater when it is okay even if the procedure causes some pain.

The side wall portion 12 of the main body 120 may have four coupling holes 120b and 120c each formed to couple the main body 120 with the fixing member 130 and the housing 200. This exemplary embodiment shows only the four coupling holes 120b and 120c. However, the present invention is not limited thereto, may have various number of coupling holes for coupling the above components to each other.

The fixing member 130 may be coupled to the main body 120, and may fix one end portion of the needle 110 thereto.

A specific structure of the fixing member 130 is hereinafter described in detail with reference to the drawings.

Figure 3:
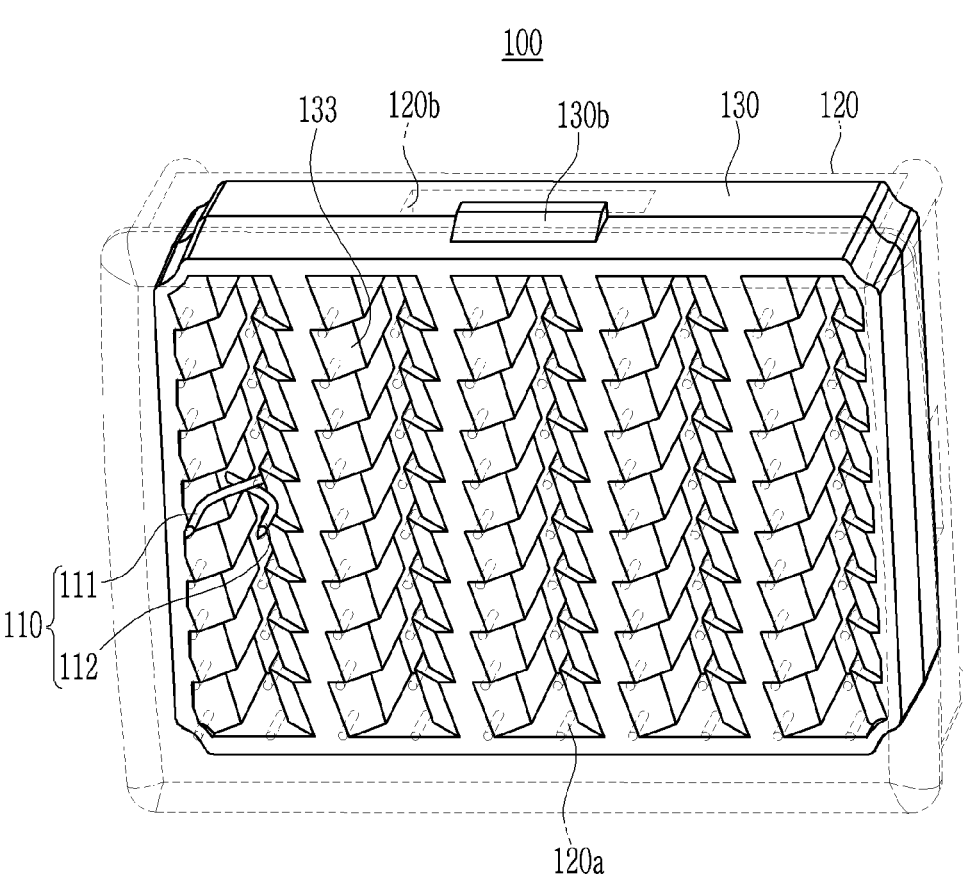
FIG. 3 is a perspective view of a needle assembly according to an exemplary embodiment of the present invention.
Figure 4:
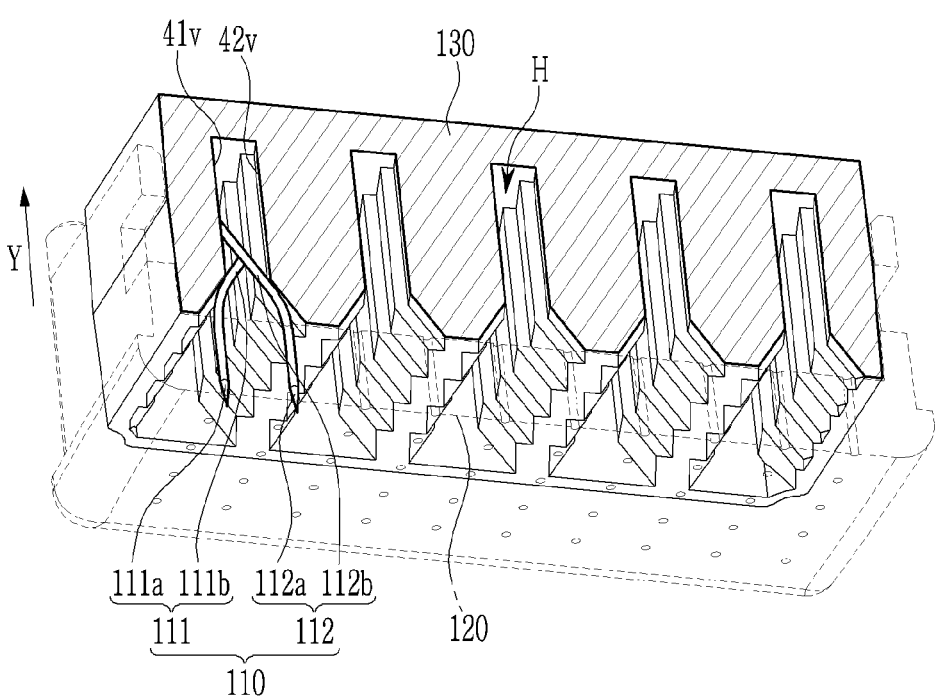
FIG. 4 is a partially cut-away perspective view of FIG. 3.
Figure 5:
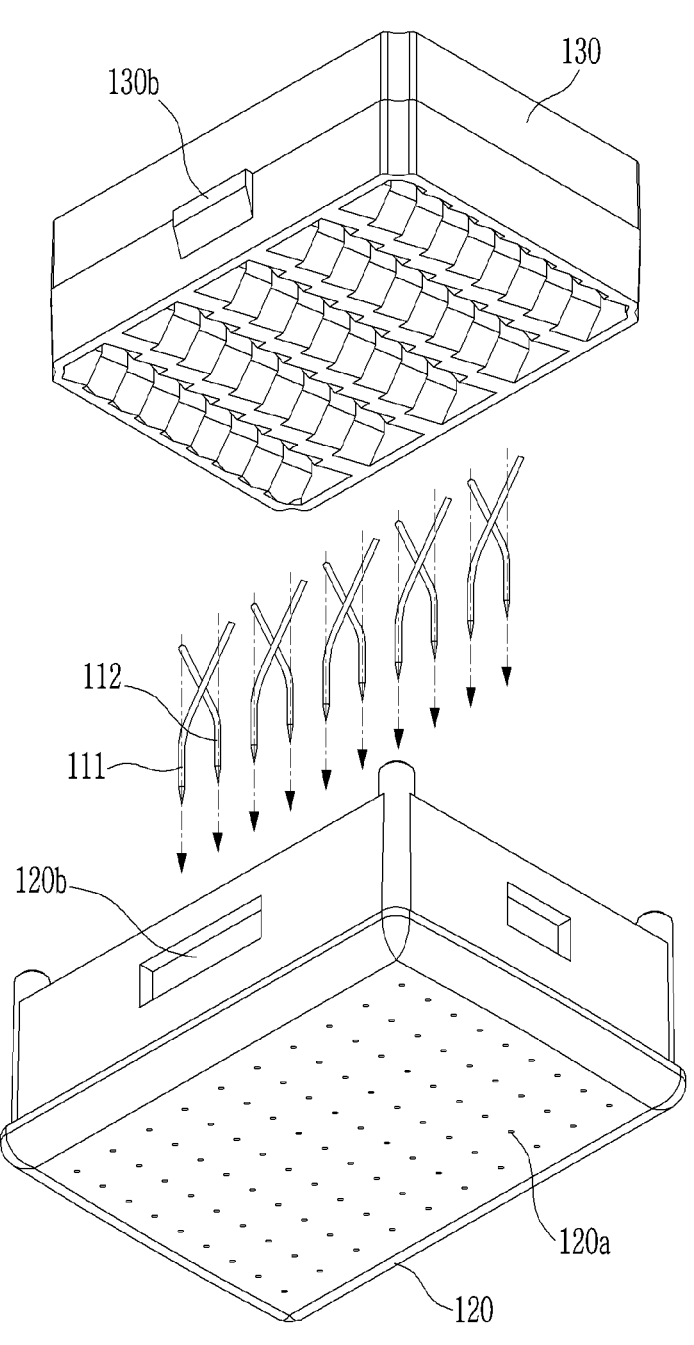
FIG. 5 is an exploded perspective view of FIG. 3.

FIG. 3 is a perspective view of a needle assembly according to an exemplary embodiment of the present invention; FIG. 4 is a partially cut-away perspective view of FIG. 3; and FIG. 5 is an exploded perspective view of FIG. 3.

Figure 6:
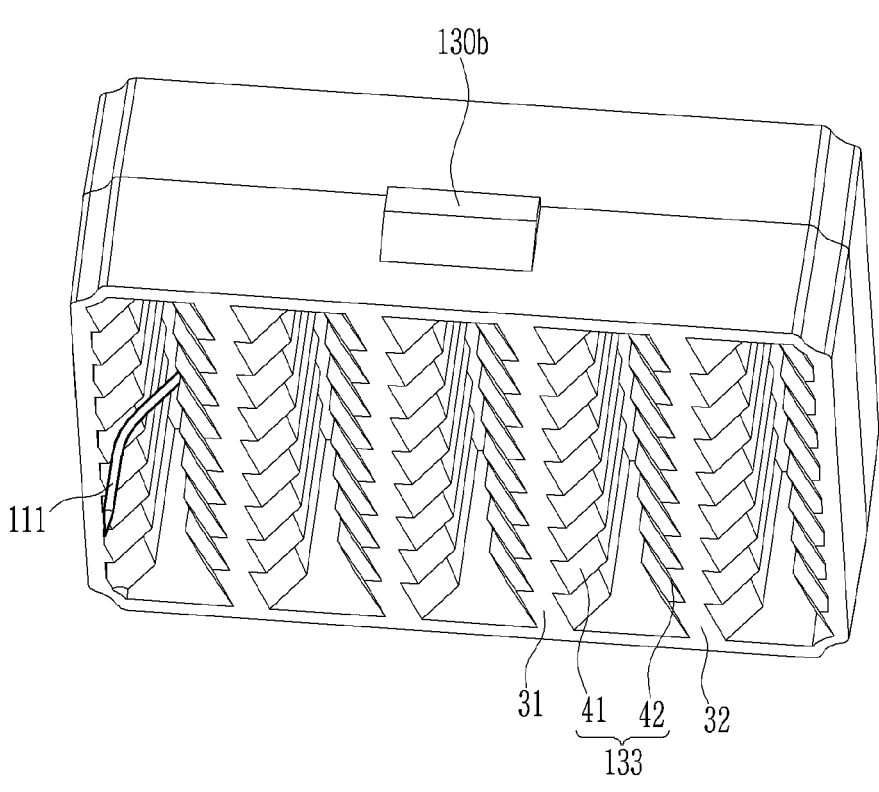
FIG. 6 is a detailed perspective view showing a position where the needle is coupled to a fixing member of FIG. 3.
Figure 7:
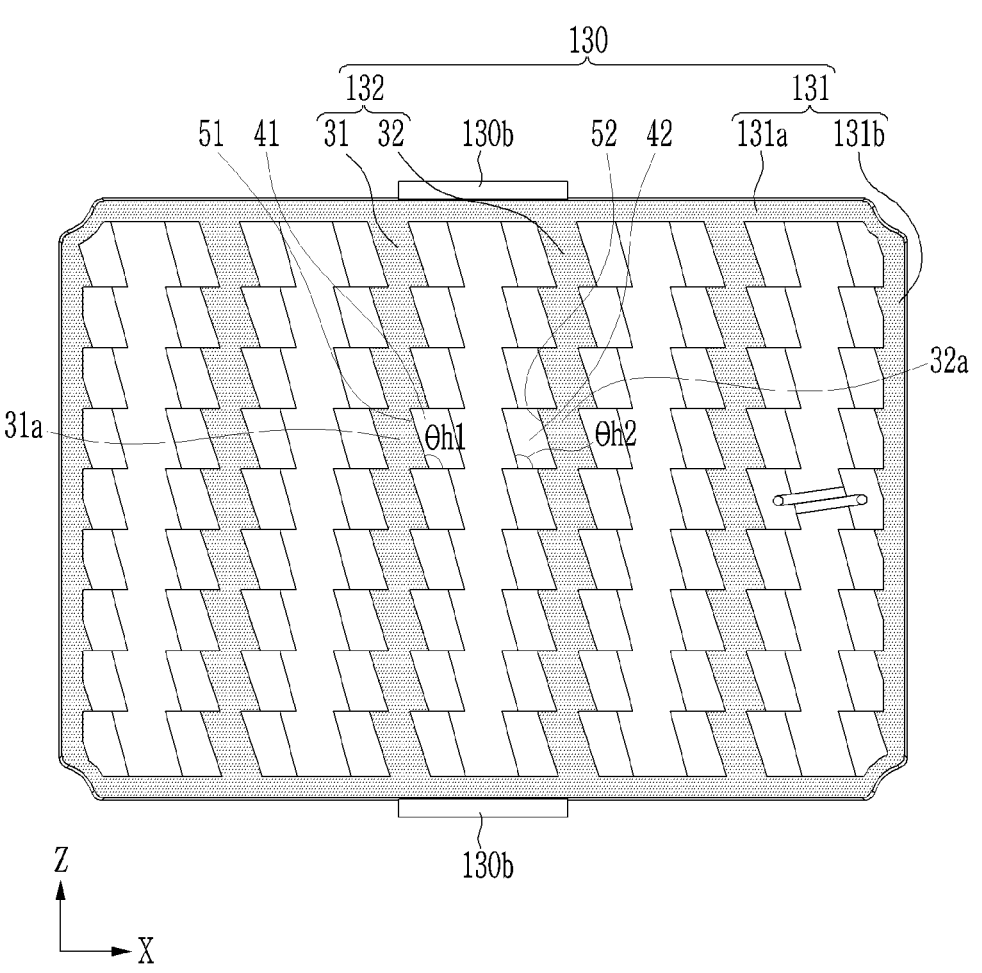
FIG. 7 is a plan view of the fixing member of FIG. 3.
Figure 8:
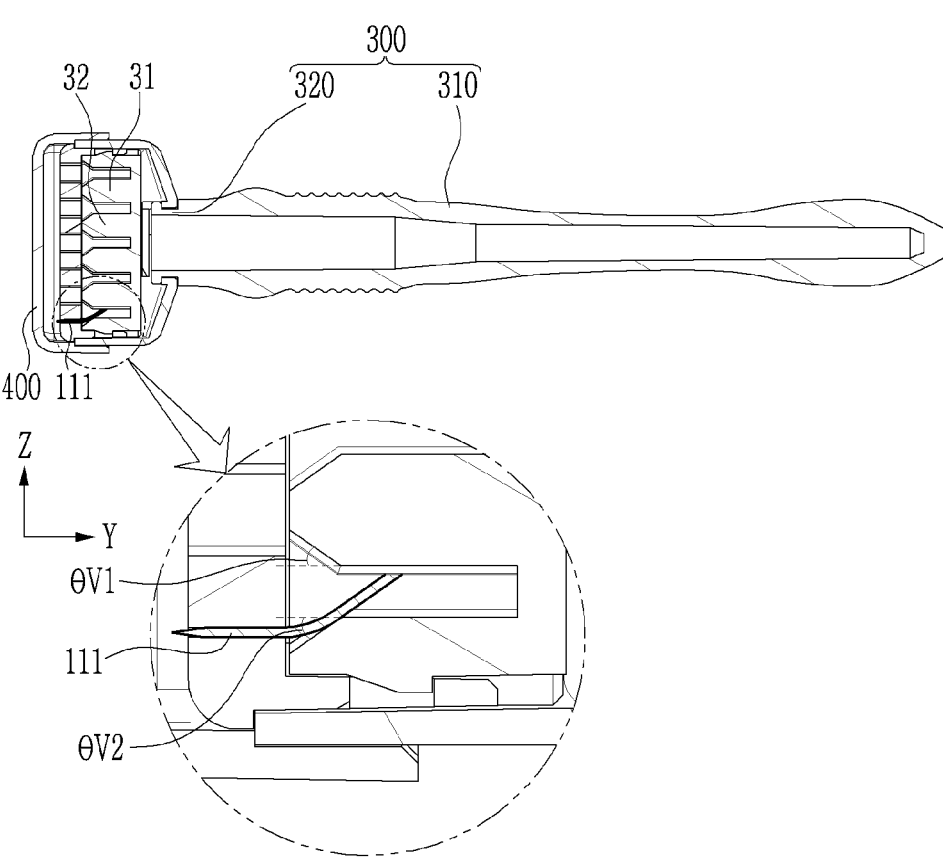
FIG. 8 is a cross-sectional view of the skin stimulator according to an exemplary embodiment of the present invention.

In addition, FIG. 6 is a detailed perspective view showing a position where the needle is coupled to a fixing member of FIG. 3; FIG. 7 is a plan view of the fixing member of FIG. 3; and FIG. 8 is a cross-sectional view of the skin stimulator according to an exemplary embodiment of the present invention.

As shown in FIGS. 3 to 8, the fixing member 130 may have a plurality of fixed inclined surfaces 133 respectively formed at positions corresponding to the holes 120a.

The needle 110 passing through the hole 120a formed in the flat main body 11 of the main body 120 may thus be bent along the fixed inclined surface 133. That is, the needle 110 may be fixed by being bent along the fixed inclined surface 133 in a portion positioned between a lower surface of the flat main body 11 and the fixed inclined surface 133. Here, the lower surface of the flat main body 11 may be a surface facing the fixing member 130.

As shown in FIG. 7, the fixing member 130 may include an outer frame 131 and a plurality of inner frames 132 positioned inside the outer frame 131 and spaced apart from each other.

The outer frame 131 may include a pair of long sides 131a and a pair of short sides 131b, respectively facing each other. The pair of long sides 131a may extend parallel to each other in a second direction X, and the pair of short sides 131b may extend parallel to each other in a third direction Z.

The plurality of fixed inclined surfaces 133 may be formed on both side surfaces of each of the inner frames 132. In addition, the inner frame 132 may extend to connect the pair of long sides 131a or the pair of short sides 131b to each other. The drawing exemplarily shows that the inner frame 132 connects between the pair of long sides 131a of the outer frame 131, that is, the inner frame 132 extends in the third direction Z, and the present invention is not limited thereto.

Meanwhile, as shown in FIGS. 3 to 8, the plurality of fixed inclined surfaces 133 may also be formed on inner surfaces of the outer frame 131, facing the inner frame. Therefore, a configuration of the fixed inclined surface 133 described below may equally be applied not only to the case where the fixed inclined surface 133 is formed on the both side surfaces of the inner frame 132 but also to the case where the fixed inclined surface 133 is formed on the inner surfaces of the outer frame 131.

The plurality of fixed inclined surfaces 133 may each be inclined by a predetermined angle in the second direction in which the plurality of inner frames 132 extend when viewed in the first direction Y. Accordingly, as shown in FIG. 7, the plurality of fixed inclined surfaces 133 may each have an approximately parallelogram shape when viewed in the first direction Y.

The plurality of inner frames 132 may include a first inner frame 31 and a second inner frame 32, which are adjacent to, spaced apart from and opposite to each other. An inner groove H (see FIG. 4) may be formed between the first inner frame 31 and the second inner frame 32.

The fixed inclined surface 133 may include a first fixed inclined surface 41 formed on the first inner frame 31 and a second fixed inclined surface 42 formed on the second inner frame 32. Here, the first fixed inclined surface 41 and the second fixed inclined surface 42 may be positioned opposite to and spaced apart from each other. Referring to FIGS. 4 and 6 together, the first fixed inclined surface 41 may extend in the first direction Y to form a first fixed vertical surface 41v on a side wall of the first inner frame 31, and the second fixed inclined surface 42 may extend in the first direction Y to form a second fixed vertical surface 42v on a side wall of the second inner frame 32.

As described above, the fixed inclined surfaces 133 may each be formed to be inclined by the predetermined angle in the direction in which the plurality of inner frames 132 extend when viewed in the first direction Y. Accordingly, as shown in FIG. 7, the fixed inclined surfaces 133 may each be inclined by first inclination angles $\theta h1$ and $\theta h2$ in the second direction X when viewed in the first direction Y. Here, the first inclination angle $\theta h1$ of the first fixed inclined surface 41 may be the same as the first inclination angle $\theta h2$ of the second fixed inclined surface 42.

Accordingly, a first upper end line 51 which is a boundary line between an upper surface 31a of the first inner frame 31 and the first fixed inclined surface 41 may be parallel to a second upper end line 52 which is a boundary line between an upper surface 32a of the second inner frame 32 and the second fixed inclined surface 42.

Here, the upper surface 31a of the first inner frame 31 and the upper surface 32a of the second inner frame 32 may refer to surfaces where the first inner frame 31 and the second inner frame 32 respectively face the main body 120.

The needle 110 may include a pointed tip portion 110a and the other end portion 110b fixed to the side wall of the inner frame 132. The needles 110 may include a first needle 111 and a second needle 112, which are opposite to each other.

The first needle 111 bent along the first fixed inclined surface 41 may be parallel to the second needle 112 bent along the second fixed inclined surface 42. The reason is that the first fixed inclined surface 41 and the second fixed inclined surface 42 may be inclined by the same angles (i.e., the first inclination angles) in the direction in which the plurality of inner frames 132 extend when viewed in the first direction Y. Therefore, the first needle 111 and the second needle 112 bent in opposite directions may not overlap with each other.

Referring to FIGS. 7 and 8, the first fixed inclined surface 41 and the second fixed inclined surface 42 may respectively form second inclination angles θv1 and θv2 in the first direction Y. Here, an absolute value of the second inclination angle θv1 formed by the first fixed inclined surface 41 in the first direction Y may be the same as an absolute value of the second inclination angle θv2 formed by the second fixed inclined surface 42 in the first direction.

The first needle 111 and the second needle 112 may thus be fixed uniformly.

A first coupling protrusion 130*b* may be formed outside the outer frame 131 of the fixing member 130. Accordingly, one coupling hole 120*b* of the main body 120 and the first coupling protrusion 130*b* may be coupled to each other, thereby coupling the main body 120 and the fixing member 130 to each other.

The housing 200 may include a housing frame 210 forming an inner space of the housing to have a shape corresponding to that of the needle assembly 100, and a second coupling protrusion 200*a* formed inside the housing frame 210.

The second coupling protrusion 200*a* may be formed at a position corresponding to the other coupling hole 120*c* of the main body 120, and coupled with the other coupling hole 120*c* of the main body 120, thereby coupling the main body 120 and the housing 200 to each other.

The handle 300 may include a handle body 310 and a fastening member 320 connecting the handle body 310 to the housing 200. The fastening member 320 may fasten the handle body 310 to the housing 200 by screwing, etc.

The assembly cover 400 may serve to cover the needle 110, may be larger than the side wall portion 12 of the main body 120, and may be fitted into the needle assembly 100. Therefore, it is possible to safely protect the tip portion of the needle 110 by using the assembly cover 400.

A manufacturing method of a skin stimulator according to an exemplary embodiment of the present invention is hereinafter described in detail with reference to the drawings.

Figure 9:
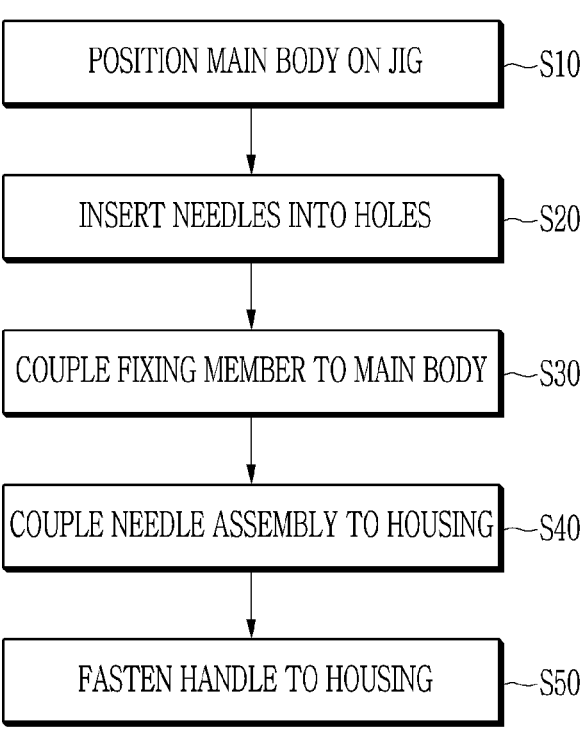
FIG. 9 is a flowchart showing a manufacturing method of a skin stimulator according to an exemplary embodiment of the present invention.
Figure 10:
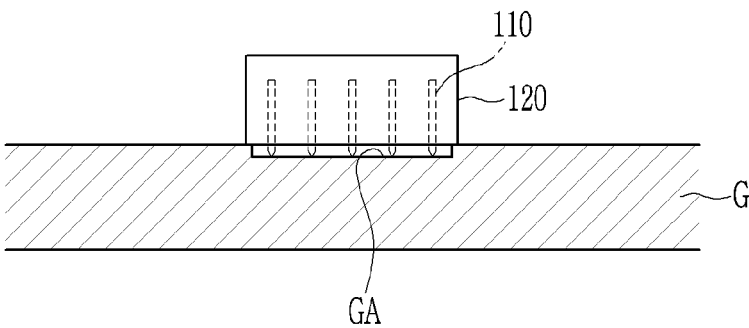
FIG. 10 is a view showing a step of the manufacturing method of a skin stimulator according to an exemplary embodiment of the present invention.

FIG. 9 is a flowchart showing a manufacturing method of a skin stimulator according to an exemplary embodiment of the present invention; and FIG. 10 is a view showing a step of the manufacturing method of a skin stimulator according to an exemplary embodiment of the present invention.

As shown in FIGS. 9 and 10, in the manufacturing method of the skin stimulator according to an exemplary embodiment of the present invention, a main body 120 having a plurality of holes 120*a* may first be positioned on a jig G of a flat plate type (S10). That is, the main body 120 may be positioned in a jig groove GA of the jig G, in a state in which one surface of the flat main body 11, having the lattice-shaped holes 120*a* formed therein, faces downward.

Next, a plurality of needles 110 may be inserted into the holes 120*a* (S20). Here, a tip portion of the needle 110 may protrude in a range of 0.2 mm to 0.24 mm by the jig groove GA of the jig G. That is, the jig groove GA may have a depth corresponding to a length at which the tip portion of the needle 110 protrudes.

Next, a fixing member 130 fixing the plurality of needles 110 may be coupled to the main body 120 to manufacture a needle assembly 100 (S30).

Here, the fixing member 130 having a plurality of fixed inclined surfaces 133 respectively formed at positions corresponding to the holes 120*a* may make the plurality of needles 110 bent along the fixed inclined surface 133.

Accordingly, the plurality of needles 110 may each be firmly supported on and bent along the fixed inclined surface 133, and the plurality of needles 110 may thus be fixed by the fixing member 130.

A first needle 111 may include a pointed tip portion 111*a* and the other end portion 111*b* in a direction opposite thereto, and a second needle 112 may include a pointed tip portion 112*a* and the other end portion 112*b* in a direction opposite thereto. Here, the other end portion 111*b* of the first needle 111 may be more firmly supported in contact with a second fixed vertical surface 42*v*, and the other end portion 112*b* of the second needle 112 may be more firmly supported in contact with a first fixed vertical surface 41*v* (see FIG. 4).

In this manner, when the fixing member 130 is coupled to the main body 120, the plurality of fixed inclined surfaces 133 may press the first needle 111 and the second needle 112 to make the first needle 111 and the second needle 112 bent. In addition, when the first needle 111 and the second needle 112 are respectively supported by a first fixed inclined surface 41 and a second fixed inclined surface 42, the first needle 111 and the second needle 112 may each be fixed in a bent state due to elasticity of the first needle 111 and the second needle 112.

Next, the needle assembly 100 may be coupled to the housing 200 (S40). Here, the needle assembly 100 may be coupled to the housing 200 except for the one surface of the flat main body 11, having the holes 120*a* formed therein.

Here, the coupling holes 120*b* and 120*c* of the main body 120 may be coupled with a first coupling protrusion 130*b* of the fixing member 130 and a second coupling protrusion 200*a* of the housing 200, thereby firmly coupling the needle assembly 100 to the housing 200.

Next, a handle 300 may be detachably fastened to the housing 200 (S50). Here, the handle 300 may be fastened to the housing 200 by screwing, etc.

Meanwhile, another exemplary embodiment is possible in which a separate electrode unit is installed in the needle assembly of an exemplary embodiment to have an improved substance absorption rate.

A skin stimulator according to another exemplary embodiment of the present invention is hereinafter described in detail with reference to FIGS. 11 and 12.

Figure 11:
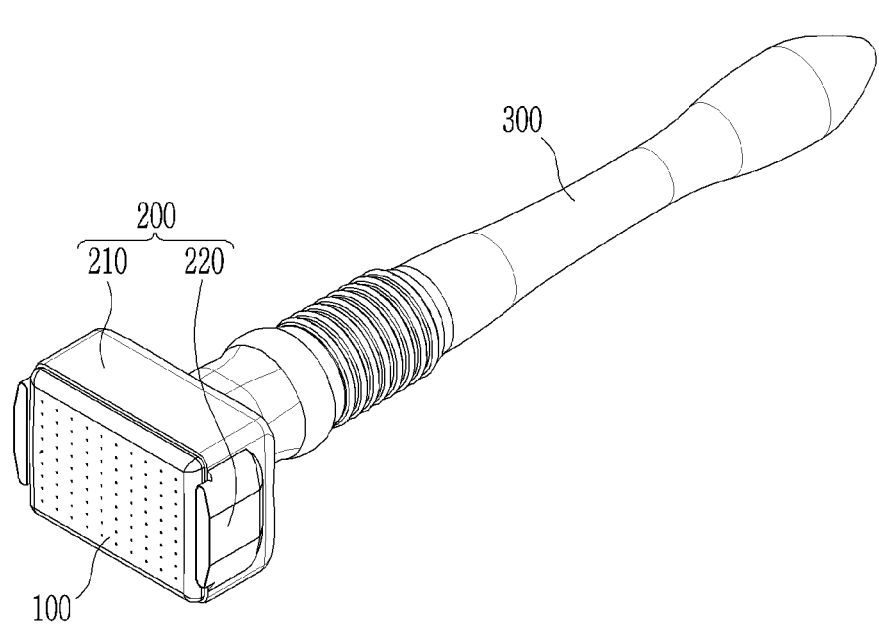
FIG. 11 is a perspective view of a skin stimulator according to another exemplary embodiment of the present invention.
Figure 12:
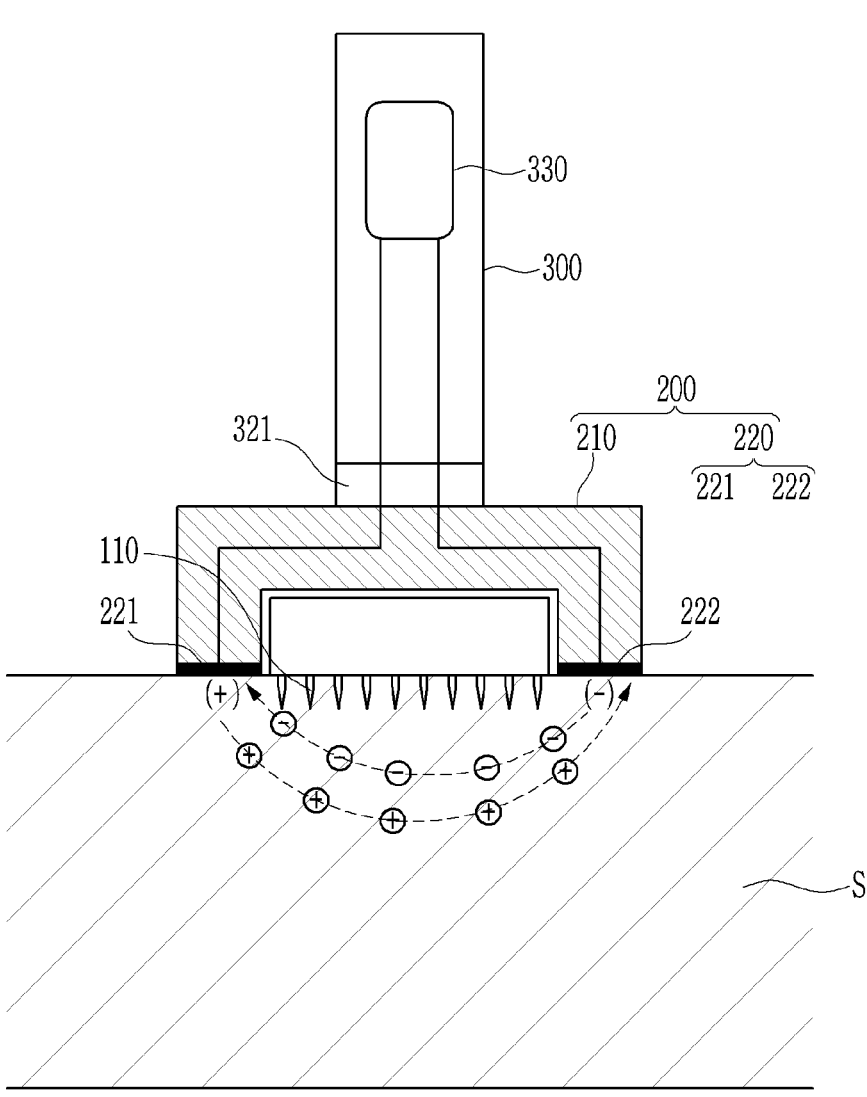
FIG. 12 is a cross-sectional view showing an operation of the skin stimulator according to another exemplary embodiment of the present invention.

FIG. 11 is a perspective view of the skin stimulator according to another exemplary embodiment of the present invention; and FIG. 12 is a cross-sectional view showing an operation of the skin stimulator according to another exemplary embodiment of the present invention.

Another exemplary embodiment shown in FIGS. 11 and 12 is substantially the same except for a structure of the electrode unit as compared with an exemplary embodiment shown in FIGS. 1 to 8, and its redundant description is thus omitted.

As shown in FIGS. 11 and 12, the skin stimulator according to another exemplary embodiment of the present invention may include the needle assembly 100 having the plurality of needles 110, the housing 200 seating the needle assembly 100 therein, the handle 300 detachably coupled to the housing 200 and the assembly cover 400 (see FIG. 1) covering the needle assembly 100.

The housing 200 may include the housing frame 210 having the shape corresponding to that of the needle assembly 100, the second coupling protrusion 200*a* (see FIG. 2) formed inside the housing frame 210, and an electrode unit 220 installed in the housing frame 210.

The electrode unit 220 may include a positive electrode unit 221 and a negative electrode unit 222 respectively positioned on both sides of the needle assembly 100. The electrode unit 220 may be disposed on the same plane as a surface of the flat main body 11 (see FIG. 2) of the main body 120. Therefore, the electrode unit 220 may easily come into contact with skin S.

The electrode unit 220 may be installed outside the housing frame 210 as shown in FIG. 11, or may be installed inside the housing frame 210 as shown in FIG. 12.

The electrode unit 220 may increase an effect of the skin stimulator by using an iontophoresis phenomenon.

The iontophoresis is a system that promotes the substance to be absorbed into the dermal layer by using electricity when an external stimulation is applied to the skin. The iontophoresis may promote the substance to penetrate into the skin by using a force in which a positive charge is moved from the positive electrode unit to the negative electrode and a negative charge is moved from the negative electrode to the positive electrode unit in an electric field generated between the positive electrode unit 221 and the negative electrode unit 222. As such, the positive electrode unit 221 and the negative electrode unit 222 may respectively be disposed on the both sides of the needle assembly 100. In this manner, it is possible to realize a function of the iontophoresis, thereby forming a closed circuit including the skin S of a user, the positive electrode unit 221 and the negative electrode unit 222. The medicine substance may thus effectively penetrate into the skin by allowing the negative charge or the positive charge to be moved. However, there may be a very low ratio at which the substance penetrates through the stratum corneum layer of the skin when using only the iontophoresis. It may thus be difficult for the medicine substance applied to the skin to penetrate through the stratum corneum layer of the skin and be effectively absorbed into the dermal layer.

However, in another exemplary embodiment of the present invention, the iontophoresis may be performed while the needle is used to pierce the stratum corneum layer of the skin, which has a very low ratio of the substance absorption, thereby making a micro-channel therethrough. In this manner, the substance that penetrated through the stratum corneum layer of the skin may penetrate into and be effectively absorbed into the dermal layer through the epidermal layer.

The handle 300 may include the handle body 310, the fastening member 320 connecting the handle body 310 to the housing 200, and a power supply unit 330 formed on the handle body 310 and supplying power to the electrode unit. Here, the power supply unit 330 may be a battery.

The fastening member 320 may fasten the handle body 310 to the housing 200 by screwing, etc. Here, the fastening member 320 may include an electrical connection member 321 maintaining an electrical connection between the handle body 310 and the housing 200 even when the handle body 310 is physically separated from the housing 200. The electrical connection member 321 may be a contact substrate, an electrical connection terminal, a conductive contact pin, a spring, etc.

The power supply unit 330 may supply power to the electrode unit 220, thereby allowing the electrode unit 220 to apply a current to the skin of the user. Therefore, the iontophoresis may cause the movements of the positive charge and the negative charge in the skin, thereby improving the ratio at which the substance is absorbed into the skin.

While the present invention has been described in connection with what is presently considered to be practical exemplary embodiments, it is to be understood that the present invention is not limited to the disclosed exemplary embodiments. On the contrary, it is intended to cover various modifications and equivalent arrangements included within the scope of the appended claims.

The invention claimed is:

1. A needle assembly comprising:
a plurality of needles;
a main body having a plurality of holes through which the plurality of needles pass in a first direction; and
a fixing member coupled to the main body and having a plurality of fixed inclined surfaces supporting the plurality of needles,
wherein the plurality of needles are supported on the plurality of fixed inclined surfaces and bent along the plurality of fixed inclined surfaces, and
a middle portion of the needle contacts the fixed inclined surfaces,
wherein tip portions of a pair of adjacent needles pass through the holes parallel to each other, and other end portions of the pair of adjacent needles cross each other and are supported by the fixed inclined surfaces.

2. The needle assembly of claim 1, wherein
the plurality of fixed inclined surfaces are respectively formed at positions corresponding to the plurality of holes.

3. The needle assembly of claim 1, wherein
the fixing member includes an outer frame coupled to the main body and a plurality of inner frames disposed parallel to and spaced apart from each other inside the outer frame, and
the plurality of fixed inclined surfaces are formed on both side surfaces of each of the plurality of inner frames.

4. The needle assembly of claim 3, wherein
the outer frame includes a pair of long sides and a pair of short sides, respectively facing each other,
the plurality of inner frames extend to connect the pair of long sides or pair of short sides of the outer frame to each other, and the plurality of fixed inclined surfaces are each inclined by a first inclination angle in a second direction in which the plurality of inner frames extend when viewed in the first direction.

5. The needle assembly of claim 4, wherein
the plurality of inner frames include a first inner frame and a second inner frame, which are adjacent to and opposite to each other, the plurality of fixed inclined surfaces include a first fixed inclined surface and a second fixed inclined surface respectively formed on opposite side surfaces of the first inner frame and the second inner frame, and
second inclination angles respectively formed by the first fixed inclined surface and the second fixed inclined surface in the first direction have the same absolute value as each other.

6. The needle assembly of claim 5, wherein
a first needle bent along the first fixed inclined surface 5 is parallel to a second needle bent along the second fixed inclined surface.

7. The needle assembly of claim 1, wherein
the main body includes
a flat main body having the plurality of holes, and
a side wall portion extending from an edge of the flat main body to form an accommodation space accommodating the fixing member and having a plurality of coupling holes, and
a first coupling protrusion coupled to at least one of the plurality of coupling holes is formed outside the fixing member.

8. A skin stimulator comprising:

a needle assembly including a plurality of needles, a flat main body having a plurality of holes through which the plurality of needles pass in a first direction, and a fixing member coupled to the main body and having a plurality of fixed inclined surfaces supporting the plurality of needles;

a housing having an inner space in which the needle assembly is seated; and a handle detachably coupled to the housing, wherein the plurality of needles are supported on the plurality of fixed inclined surfaces and bent along the plurality of fixed inclined surfaces, and a middle portion of the needle contacts the fixed inclined surfaces, wherein tip portions of a pair of adjacent needles pass through the holes parallel to each other, and other end portions of the pair of adjacent needles cross each other and are supported by the fixed inclined surfaces.

9. The skin stimulator of claim 8, wherein the needle assembly has a plurality of coupling holes coupling the needle assembly to the housing, and a second coupling protrusion coupled to at least one of the plurality of 10 coupling holes is formed inside the housing.

10. The skin stimulator of claim 8, wherein the housing includes a housing frame forming the inner space, and an electrode unit installed in the housing frame and disposed on the same plane as a surface of the flat main body.

11. The skin stimulator of claim 10, wherein the electrode unit includes a positive electrode unit and a negative electrode unit respectively positioned on both sides of the needle assembly.

12. The skin stimulator of claim 10, wherein the handle includes a power supply unit supplying power to the electrode unit.

13. A manufacturing method of a skin stimulator, the method comprising:

positioning a main body having a plurality of holes on a jig;

inserting a plurality of needles into the plurality of holes;

coupling a fixing member to the main body while pressing the plurality of needles by using the fixing member;

coupling a needle assembly, in which the fixing member and the main body are coupled to each other, to a housing; and detachably fastening a handle to the housing, wherein the fixing member has a plurality of fixed inclined surfaces respectively formed at positions corresponding to the plurality of holes, and in the coupling of the fixing member to the main body, the plurality of needles are bent along and fixed to the plurality of fixed inclined surfaces, and a middle portion of the needle contacts the fixed inclined surfaces, wherein tip portions of a pair of adjacent needles pass through the holes parallel to each other, and other end portions of the pair of adjacent needles cross each other and are supported by the fixed inclined surfaces.

* * * * *